(12) United States Patent
Chang et al.

(10) Patent No.: US 11,851,387 B2
(45) Date of Patent: Dec. 26, 2023

(54) PARA-PHENYLENEDIAMINE DERIVATIVE, 1,4-CYCLOHEXYLDIAMINE DERIVATIVE, AND FABRICATING METHOD FOR 1,4-DIAMINE CYCLIC COMPOUND DERIVATIVE

(71) Applicant: Yuanhan Materials Inc., Taipei (TW)

(72) Inventors: En Ming Chang, Taipei (TW); Hung-Chun Yu, Taipei (TW); Feng-Chao Yu, Taipei (TW)

(73) Assignee: Yuanhan Materials Inc., Taipei (TW)

( * ) Notice: Subject to any disclaimer, the term of this patent is extended or adjusted under 35 U.S.C. 154(b) by 0 days.

(21) Appl. No.: 17/811,872

(22) Filed: Jul. 11, 2022

(65) Prior Publication Data

US 2023/0075418 A1    Mar. 9, 2023

(30) Foreign Application Priority Data

Aug. 18, 2021    (TW) ................................. 110130465

(51) Int. Cl.
    *C07C 209/36*    (2006.01)

(52) U.S. Cl.
    CPC .................. *C07C 209/36* (2013.01)

(58) Field of Classification Search
    CPC .................................................. C07C 209/36
    See application file for complete search history.

(56) References Cited

U.S. PATENT DOCUMENTS

| | | |
|---|---|---|
| 3,965,183 A | 6/1976 | Gay et al. |
| 4,754,069 A | 6/1988 | Braun et al. |
| 6,503,282 B1 | 1/2003 | Braun |

(Continued)

FOREIGN PATENT DOCUMENTS

| | | |
|---|---|---|
| CN | 1102572 C | 3/2003 |
| CN | 101774929 A | 7/2010 |

(Continued)

OTHER PUBLICATIONS

A. Ono et al., 51 Bulletin of the Chemical Society of Japan, 3083-3084 (1978) (Year: 1978).*

(Continued)

*Primary Examiner* — Alexander R Pagano
(74) *Attorney, Agent, or Firm* — CKC & Partners Co., LLC

(57) ABSTRACT

A fabricating method for a 1,4-diamine cyclic compound derivative includes: performing a first thermal process to form a first compound, in which the first compound has a structure represented by formula (i):

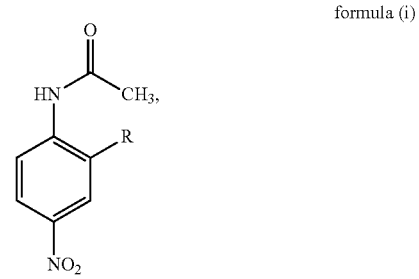

formula (i)

in which R represents a C1 to C12 hydrocarbon group; performing a second thermal process, which includes performing a reduction reaction on the first compound to form a second compound, in which the second compound has a structure represented by formula (ii),

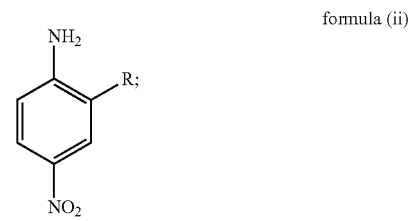

formula (ii)

and performing a third thermal process, which includes performing a reduction reaction on the second compound to form the 1,4-diamine cyclic compound derivative, in which the 1,4-diamine cyclic compound derivative has a structure represented by formula (I) or formula (II):

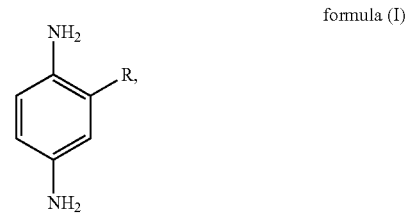

formula (I)

in which R represents a C1 to C12 hydrocarbon group,

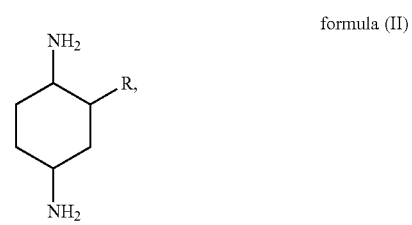

formula (II)

in which R represents a C1 to C12 hydrocarbon group.

5 Claims, 2 Drawing Sheets

(56) References Cited

U.S. PATENT DOCUMENTS

| | | | |
|---|---|---|---|
| 6,635,091 B2* | 10/2003 | Saunier | A61K 8/42 8/408 |
| 6,849,766 B2* | 2/2005 | Chassot | C07C 211/51 8/408 |
| 6,916,346 B2 | 7/2005 | Lim et al. | |
| 7,833,685 B2* | 11/2010 | Tanaka | C09B 29/0003 430/108.23 |
| 10,870,724 B2* | 12/2020 | Peters | C08G 59/245 |
| 2003/0121110 A1 | 7/2003 | Chassot et al. | |
| 2013/0123540 A1* | 5/2013 | Goettel | C07C 209/36 564/305 |
| 2019/0092717 A1 | 3/2019 | Lim et al. | |
| 2020/0239635 A1* | 7/2020 | McNamara | C08G 73/1082 |
| 2020/0247749 A1 | 8/2020 | Murphy | |

FOREIGN PATENT DOCUMENTS

| | | |
|---|---|---|
| CN | 101502800 B | 7/2011 |
| CN | 103787908 A | 5/2014 |
| CN | 102285891 B | 6/2014 |
| CN | 103086878 B | 3/2015 |
| CN | 104844461 A | 8/2015 |
| CN | 106693960 A | 5/2017 |
| CN | 106543017 B | 4/2018 |
| CN | 109867604 A | 6/2019 |
| CN | 110167916 A | 8/2019 |
| CN | 111542304 A | 8/2020 |
| GB | 990797 A * | 5/1965 |
| JP | 63238120 A * | 10/1988 |
| JP | H63238120 A | 10/1988 |
| TW | 201224003 A | 6/2012 |

OTHER PUBLICATIONS

R. Nallagonda et al., 16 Organic Letters, 4786-4789 (2014) (Year: 2014).*

Corresponding Taiwan office action dated Nov. 21, 2022.

The Office Action of corresponding TW application dated Apr. 20, 2023.

* cited by examiner

PARA-PHENYLENEDIAMINE DERIVATIVE, 1,4-CYCLOHEXYLDIAMINE DERIVATIVE, AND FABRICATING METHOD FOR 1,4-DIAMINE CYCLIC COMPOUND DERIVATIVE

RELATED APPLICATION

This application claims priority to Taiwan Application Serial Number 110130465, filed Aug. 18, 2021, which is herein incorporated by reference.

BACKGROUND

Field of Invention

The present disclosure relates to a para-phenylenediamine derivative, a 1,4-cyclohexyldiamine derivative, and a fabricating method for a 1,4-diamine cyclic compound derivative.

Description of Related Art

In recent years, the field of flexible displays has been an important development direction for the electronic information industry. Since flexible displays have advantages such as impact resistance, shock resistance, light weight, small size, and portability, flexible displays have broad market prospects. Polyimide resin, which has the characteristics of high and low temperature resistance, radiation resistance, and chemical resistance, is a common material used in the field of flexible displays. However, currently common monomers used to synthesize polyimide resins (e.g., para-phenylenediamine and 1,4-diamine cyclic compounds) often result in the precipitation of salts at the initial stage of the polymerization reaction due to their low solubility, resulting in that the polymerization reaction is terminated or the reaction time is prolonged, which limit the molecular weight of the polymer (i.e., polyimide resin). Based on the above, how to provide a monomer with good solubility and reactivity to facilitate the polymerization of polyimide resins is an important issue for the researchers in the field.

SUMMARY

According to some embodiments of the present disclosure, a para-phenylenediamine derivative has a structure represented by formula (I):

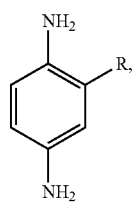

formula (I)

in which R represents a C1 to C12 hydrocarbon group.

In some embodiments of the present disclosure, in the structure represented by formula (I), R represents a C1 to C12 alkyl group.

In some embodiments of the present disclosure, in the structure represented by formula (I), R represents a C1 to C12 linear alkyl group.

According to some embodiments of the present disclosure, a 1,4-cyclohexanediamine derivative has a structure represented by formula (II):

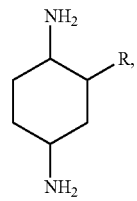

formula (II)

in which R represents a C1 to C12 hydrocarbon group.

In some embodiments of the present disclosure, in the structure represented by formula (II), R represents a C1 to C12 alkyl group.

In some embodiments of the present disclosure, in the structure represented by formula (II), R represents a C1 to C12 linear alkyl group.

According to some embodiments of the present disclosure, a fabricating method for a 1,4-diamine cyclic compound derivative includes: performing a first thermal process which includes using monohydric alcohol and para-toluenesulfonic acid for an addition reaction of para-nitroacetaniline, such that a first compound is formed, in which the monohydric alcohol has a C1 to C12 hydrocarbon group, and the first compound has a structure represented by formula (i):

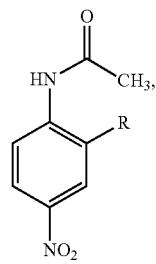

formula (i)

in which R represents a C1 to C12 hydrocarbon group; performing a second thermal process which includes performing a reduction reaction on the first compound, such that a second compound is formed, in which the second compound has a structure represented by formula (ii),

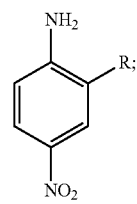

formula (ii)

and performing a third thermal process which includes performing a reduction reaction on the second compound, such that the 1,4-diamine cyclic compound derivative is formed, in which the 1,4-diamine cyclic compound derivative has a structure represented by formula (I) or formula (II):

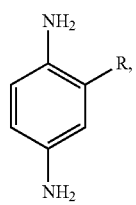

formula (I)

in which R represents a C1 to C12 hydrocarbon group,

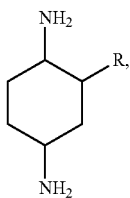

formula (II)

in which R represents a C1 to C12 hydrocarbon group.

In some embodiments of the present disclosure, the third thermal process includes using hydrogen to perform the reduction reaction on the second compound, and when the 1,4-diamine cyclic compound derivative has the structure represented by formula (I), a pressure of the third thermal process is between 14 psi and 15 psi, a temperature of the third thermal process is between 25° C. and 40° C., and based on 1 equivalence of the second compound, an equivalence of the hydrogen is between 2.5 and 4.

In some embodiments of the present disclosure, the third thermal process comprises using hydrogen to perform the reduction reaction on the second compound, and when the 1,4-diamine cyclic compound derivative has the structure represented by formula (II), a pressure of the third thermal process is between 600 psi and 800 psi, a temperature of the third thermal process is between 100° C. and 140° C., and based on 1 equivalence of the second compound, an equivalence of the hydrogen is between 7 and 8.

In some embodiments of the present disclosure, based on 1 equivalence of the para-nitroacetaniline, an equivalence of the para-toluenesulfonic acid is between 1.1 and 1.5.

In the aforementioned embodiments of the present disclosure, the para-phenylenediamine derivative and the 1,4-cyclohexanediamine derivative of the present disclosure can be applied to the field of flexible displays to play the role of monomers of polymers (e.g., polyimide). Through the respective molecular structure designs of the para-phenylenediamine derivative and the 1,4-cyclohexanediamine derivative, the para-phenylenediamine derivative and the 1,4-cyclohexanediamine derivative can have good solubility to facilitate the subsequent polymerization reaction. In addition, the para-phenylenediamine derivative or the 1,4-cyclohexanediamine derivative can be selectively obtained through the control of the reaction conditions during the fabricating method for the 1,4-diamine cyclic compound derivative of the present disclosure. Accordingly, the desired product can be selectively obtained through the switching of reaction conditions in a single fabricating method, such that the convenience of fabricating monomers is improved, and the production costs are reduced.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
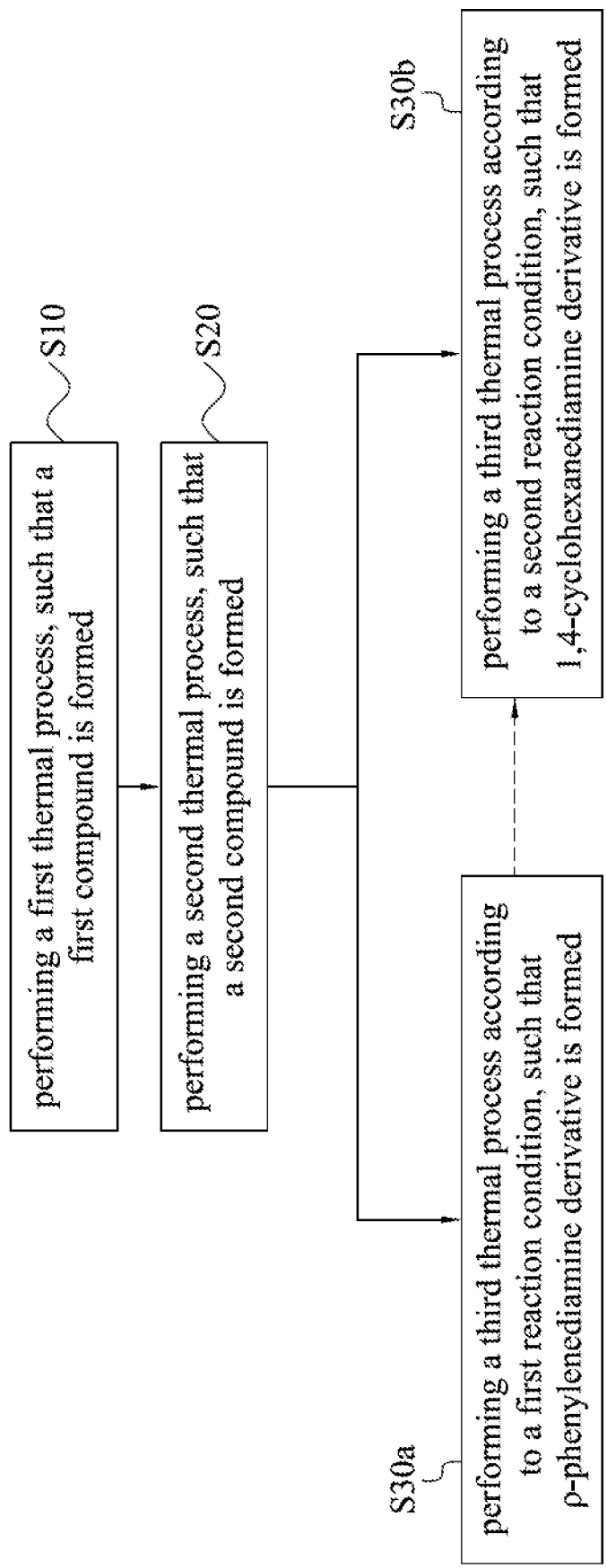
FIG. 1 is a flow diagram illustrating a fabricating method for a 1,4-diamine cyclic compound derivative according to some embodiments of the present disclosure.

Reference will now be made in detail to the present embodiments of the disclosure, examples of which are illustrated in the accompanying drawings. Wherever possible, the same reference numbers are used in the drawings and the description to refer to the same or like parts.

In the present disclosure, the structure of a polymer or a functional group is sometimes represented by a skeleton formula. This representation can omit carbon atoms, hydrogen atoms, and carbon-hydrogen bonds. Certainly, if the atom or atom group is clearly drawn in the structural formula, the drawing shall prevail.

The present disclosure provides a para-phenylenediamine derivative and a 1,4-cyclohexanediamine derivative, which can be applied to the field of flexible displays, such as flexible E-paper, flexible active matrix organic light-emitting diode (flexible AMOLED), flexible liquid crystal display (flexible LCD), and flexible lighting, to play the role of monomers of polymers, in which the polymers can be polyimide commonly used in the field of flexible displays. Through the respective molecular structure designs of the para-phenylenediamine derivative and the 1,4-cyclohexanediamine derivative, the para-phenylenediamine derivative and the 1,4-cyclohexanediamine derivative can have good solubility to facilitate the subsequent polymerization reaction. On the other hand, the present disclosure further provides a fabricating method for a 1,4-diamine cyclic compound derivative, by which the para-phenylenediamine derivative or the 1,4-cyclohexanediamine derivative can be selectively obtained through the control of the reaction conditions. Accordingly, the desired product (the para-phenylenediamine derivative or the 1,4-cyclohexanediamine derivative) can be selectively obtained through the switching of reaction conditions in a single fabricating method, such that the convenience of fabricating monomers is improved, and the production costs are reduced.

FIG. 1 is a flow diagram illustrating a fabricating method for a 1,4-diamine cyclic compound derivative according to some embodiments of the present disclosure. Reference is made to FIG. 1. The fabricating method for the 1,4-diamine cyclic compound derivative includes steps S10, S20, S30a, and S30b. In step S10, a first thermal process is performed, such that a first compound is formed. In step S20, a second thermal process, which includes performing a reduction reaction on the first compound, is performed, such that a second compound is formed. In step S30a, a third thermal process, which includes performing a reduction reaction on the second compound, is performed, such that a 1,4-diamine cyclic compound derivative (the para-phenylenediamine derivative) is formed. In step S30b, another third thermal process, which includes performing a reduction reaction on the second compound, is performed, such that another 1,4-diamine cyclic compound derivative (the 1,4-cyclohexanediamine derivative) is formed. In the following description, the aforementioned steps will be sequentially described.

Fabrication of the First Compound

The first compound in the present disclosure has a structure represented by formula (i):

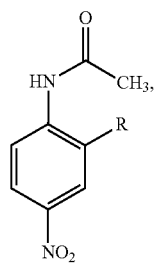

formula (i)

in which R represents a C1 to C12 hydrocarbon group, preferably represents a C1 to C12 alkyl group, and more preferably represents a C1 to C12 linear alkyl group. In the fabricating method of the first compound, firstly, para-nitroacetaniline, para-toluenesulfonic acid, monohydric alcohol, and solvent are provided. In some embodiments, based on 1 equivalence of the para-nitroacetaniline, an equivalence of the para-toluenesulfonic acid can be between 1.1 and 1.5, an equivalence of the monohydric alcohol can be between 1.0 and 1.5, and an equivalence of the solvent can be between 9 and 11. In some embodiments, the monohydric alcohol may have a C1 to C12 hydrocarbon group, preferably may have a C1 to C12 alkyl group, and more preferably may have a C1 to C12 linear alkyl group. Specifically, the type of hydrocarbon group of the monohydric alcohol may be determined according to the R group to be possessed by the first compound, that is, the type of hydrocarbon group of the monohydric alcohol corresponds to the R group of the first compound. For example, when the R group represents a C1 to C12 alkyl group, the monohydric alcohol can be methanol, ethanol, propanol, butanol, . . . , decanol, undecyl alcohol, or dodecanol. For another example, when the R group represents a C1 to C12 linear alkyl group, the monohydric alcohol can be methanol, ethanol, n-propanol, n-butanol, . . . , n-decanol, n-undecyl alcohol, n-dodecanol (also called lauryl alcohol). When the R group is a linear alkyl group, the steric hindrance contributed by the R group is small, such that the acetylamino group located on the ortho position of the R group can well react during the subsequent reactions. In some embodiments, the solvent may be dimethylformamide (DMF), such that each reagent can be well dissolved.

Then, step S10 is performed, that is, the first thermal process is performed, in which the monohydric alcohol and the para-toluenesulfonic acid are used for an addition reaction of the para-nitroacetaniline, such that the first compound is formed. In detail, during the first thermal process, the para-nitroacetaniline can undergo an addition reaction with the monohydric alcohol, such that the first compound is obtained, and the para-toluenesulfonic acid can increase the reactivity of the monohydric alcohol and can replace the strong Lewis acid required for traditional addition reactions, thereby improving the convenience of the fabricating process. In some embodiments, the monohydric alcohol can also act as a co-solvent to improve the solubility of para-nitroacetaniline in the solvent. In some embodiments, a temperature of the first thermal process can be between 80° C. and 100° C., a pressure of the first thermal process can be between 300 psi and 450 psi, and a time of the first thermal process can be between 1 hour and 1.5 hours. It should be understood that based on the Ring-Current Theory of benzene ring, the R group from a monohydric alcohol tends to be added to the 2° position of para-nitroacetaniline, such that other by-products are not easily produced. Accordingly, a yield of the first compound of the present disclosure can be greater than 90%.

Fabrication of the Second Compound

The second compound in the present disclosure has a structure represented by formula (ii):

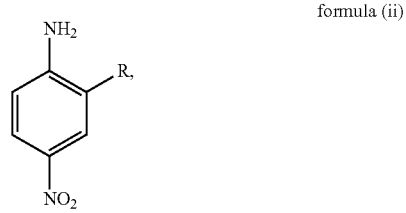

formula (ii)

in which R represents a C1 to C12 hydrocarbon group, preferably represents a C1 to C12 alkyl group, and more preferably represents a C1 to C12 linear alkyl group. In the fabricating method of the second compound, firstly, the first compound, sulfuric acid, and water are provided and uniformly mixed, such that a mixture is obtained. In some embodiments, based on 1 equivalence of the first compound, an equivalence of the sulfuric acid can be between 1.2 and 1.3, and an equivalence of the water can be between 1 and 1.1. In some embodiments, the molarity of the sulfuric acid may be between 0.5 M and 1 M, in order to improve the reactivity.

Next, step S20 is performed, that is, the second thermal process is performed, in which the first compound undergoes a reduction reaction, such that the second compound is formed. In detail, during the second thermal process, the acetylamino group of the first compound is reduced to an amino group by the sulfuric acid, such that the second compound is obtained. Specifically, during the second thermal process, the aforementioned mixture can be heated to a temperature between 60° C. and 80° C., then be refluxed under a normal pressure for 1 hour to 1.5 hours, and then undergo steps of cooling, filtration, washing, drying, etc., such that the second compound is obtained. Through the control of the above reaction conditions (e.g., reactant equivalence, reactant concentration, reaction temperature, reaction time, etc.), a yield of the second compound of the present disclosure can be greater than 85%.

Fabrication of the 1,4-Diamine Cyclic Compound Derivative

The 1,4-diamine cyclic compound derivative of the present disclosure may be the para-phenylenediamine derivative or the 1,4-cyclohexanediamine derivative, in which the para-phenylenediamine derivative has a structure represented by formula (I), and the 1,4-cyclohexanediamine derivative has a structure represented by formula (II):

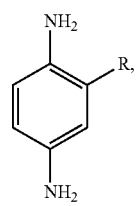

formula (I)

in which R represents a C1 to C12 hydrocarbon group, preferably represents a C1 to C12 alkyl group, and more preferably represents a C1 to C12 linear alkyl group;

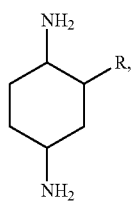

formula (II)

in which R represents a C1 to C12 hydrocarbon group, preferably represents a C1 to C12 alkyl group, and more preferably represents a C1 to C12 linear alkyl group. Regardless of the structure represented by formula (I) or formula (II), both of which can be fabricated by the aforementioned second compound, that is, the desired product (the para-phenylenediamine derivative or the 1,4-cyclohexanediamine derivative) can be selectively obtained through the switching of reaction conditions in a single fabricating method, such that the convenience of the fabricating process is improved, and the production costs are reduced. The fabricating methods of the two products will be described in detail below.

Regarding the fabricating method of the para-phenylenediamine derivative (i.e., the structure represented by formula (I)), firstly, the second compound, a catalyst, hydrogen, and solvent are provided. In some embodiments, the catalyst may be, for example, palladium on carbon (Pd/C), of which the mass percentage is about 5%. In some embodiments, based on 1 equivalence of the second compound, an equivalence of the hydrogen is between 2.5 and 4. In some embodiments, the solvent may be, for example, methanol, and based on 1 equivalence of the second compound, an equivalence of the solvent may be between 3 and 5.

Next, step S30a is performed, that is, the third thermal process is performed, in which the second compound undergoes a reduction reaction, such that the para-phenylenediamine derivative is formed. In detail, during the third thermal process, the nitro group of the second compound is reduced to an amino group by the hydrogen, such that the para-phenylenediamine derivative is obtained. Specifically, during the third thermal process, the second compound, the catalyst, and the solvent can be placed into a reaction flask and mixed thoroughly, then nitrogen and hydrogen are inserted into the reaction flask alternately for several times, then hydrogen is inserted into the reaction flask such that a reaction pressure is between 14 psi and 15 psi (a normal pressure condition), and then a reaction temperature is raised to be between 25° C. and 40° C. to react for 1.5 hours to 2.5 hours, such that the second compound undergoes a hydrogenation reaction. It should be understood that since the above reaction condition (also referred to as the first reaction condition) is relatively mild, the benzene ring of the second compound will not be affected by the hydrogenation reaction to change its structural characteristics. Through the control of the above reaction condition (equivalence of reactants, reaction pressure, reaction temperature, reaction time, etc.), a yield of the para-phenylenediamine derivative of the present disclosure can be greater than 95%.

Regarding the fabricating method of the 1,4-cyclohexanediamine derivative (i.e., the structure represented by formula (II)), firstly, the second compound, a catalyst, hydrogen, and solvent are provided. In some embodiments, the catalyst may be, for example, palladium on carbon (Pd/C), of which the mass percentage is about 5%. In some embodiments, based on 1 equivalence of the second compound, an equivalence of the hydrogen is between 7 and 8. In some embodiments, the solvent may be, for example, methanol, and based on 1 equivalence of the second compound, an equivalence of the solvent may be between 4 and 6.

Next, step S30b is performed, that is, the third thermal process is performed, in which the second compound undergoes a reduction reaction, such that the 1,4-cyclohexanediamine derivative is formed. In detail, during the third thermal process, the nitro group of the second compound is reduced to an amino group by the hydrogen, and the benzene ring of the second compound is reduced to a cyclohexane, such that the 1,4-cyclohexanediamine derivative is formed. Specifically, during the third thermal process, the second compound, the catalyst, and the solvent can be placed into a reaction flask and mixed thoroughly, then nitrogen and hydrogen are inserted into the reaction flask alternately for several times, then hydrogen is inserted into the reaction flask such that a reaction pressure is between 600 psi and 800 psi (a high pressure condition), and then the a reaction temperature is raised to be between 100° C. and 140° C. to react for 2.5 hours to 3.5 hours, such that the second compound undergoes a hydrogenation reaction. It should be understood that since the above reaction condition (also referred to as the second reaction condition) is relatively violent, the benzene ring of the second compound will be affected by the hydrogenation reaction to change its structural characteristics to form cyclohexane. Through the control of the above reaction condition (equivalence of reactants, reaction pressure, reaction temperature, reaction time, etc.), a yield of the 1,4-cyclohexanediamine derivative of the present disclosure can be greater than 90%.

Based on the above description of step S30a and step S30b, it can be seen that through the control of reaction conditions, the para-phenylenediamine derivative or the 1,4-cyclohexanediamine derivative can be selectively obtained. As a result, the desired product can be selectively obtained through the switching of reaction conditions in a single fabricating method, such that the convenience of the fabricating process is improved, and the production costs are reduced. In detail, if a polyimide with high temperature resistance (e.g., the glass transition temperature ($T_g$) of the polyimide is greater than 500° C.) is desired to be formed, the para-phenylenediamine derivative can be chosen to be fabricated to act as the monomer; and if a polyimide with high transparency is desired to be formed, the 1,4-cyclohexanediamine derivative can be chosen to be fabricated to act as the monomer. In some embodiments, if the product to be fabricated needs to be temporarily changed during the fabrication of the para-phenylenediamine derivative (that is, during the step S30a), the reaction conditions can be further switched from the first reaction condition to the second reaction condition (that is, to the step S30b), so as to obtain the 1,4-cyclohexanediamine derivative.

Since the R group of the 1,4-diamine cyclic compound derivative (including the para-phenylenediamine derivative and the 1,4-cyclohexanediamine derivative) is a C1 to C12 hydrocarbon group, the 1,4-diamine cyclic compound derivative may have good solubility to facilitate the subsequent polymerization reaction, thereby increasing the molecular weight of the polymer, so as to be well applied in the field of flexible displays. Furthermore, when the R group of the 1,4-diamine cyclic compound derivative is a C11 to C12 hydrocarbon group, the 1,4-diamine cyclic compound derivative may have better solubility. In addition, when the R group of the 1,4-diamine cyclic compound derivative is a C11 to C12 alkyl group or even a linear alkyl group, the 1,4-diamine cyclic compound derivative may have even better solubility. On the other hand, when the R group of the 1,4-diamine cyclic compound derivative is a linear alkyl group, the steric hindrance contributed by the R group is small, which can avoid interference with the amino group located on the ortho position of the R group, such that the amino group can well react during the polymerization reaction.

In the following descriptions, features and effects of the present disclosure will be described more specifically with reference to some Embodiments and some Comparative Examples. It is noted that without exceeding the scope of the present disclosure, the materials used, their amount and ratio, processing details, processing flow, etc. can be appropriately alternated. Therefore, the present disclosure should not be interpreted restrictively by the Embodiments provided below. Specifically, each Comparative Example and each Embodiment are thoroughly mixed with solvent commonly used in the synthesis of polyimide (e.g., N-methylpyrrolidone (NMP) and dimethylacetamide (DMAc)), and the solubility of each Comparative Example and each Embodiment in the solvent is measured, so as to verify the efficacy of the present disclosure. The detailed description and the measurement results of the solubility of each Comparative Example and each Embodiment are shown in Table 1.

TABLE 1

| Compound | R group | Solvent | Solubility (g/100 g solvent) |
|---|---|---|---|
| Comparative Example 1 | para-phenylenediamine derivative | N/A | NMP | 4.1 |
| Embodiment 1 | | linear methyl group | | 5.0 |
| Embodiment 2 | | linear ethyl group | | 5.5 |
| Embodiment 3 | | linear propyl group | | 5.8 |
| Embodiment 4 | | linear butyl group | | 6.0 |
| Embodiment 5 | | linear pentyl group | | 6.5 |
| Embodiment 6 | | linear hexyl group | | 6.6 |
| Embodiment 7 | | linear heptyl group | | 6.8 |
| Embodiment 8 | | linear octyl group | | 7.0 |
| Embodiment 9 | | linear nonyl group | | 7.2 |
| Embodiment 10 | | linear decyl group | | 7.3 |
| Embodiment 11 | | linear undecyl group | | 9.0 |
| Embodiment 12 | | linear dodecyl group | | 11.0 |
| Comparative Example 2 | 1,4-cyclohexanediamine derivative | N/A | DMAc | 5.7 |
| Embodiment 13 | | linear methyl group | | 6.0 |
| Embodiment 14 | | linear ethyl group | | 6.5 |
| Embodiment 15 | | linear propyl group | | 6.6 |
| Embodiment 16 | | linear butyl group | | 6.8 |
| Embodiment 17 | | linear pentyl group | | 7.0 |
| Embodiment 18 | | linear hexyl group | | 7.1 |
| Embodiment 19 | | linear heptyl group | | 7.2 |
| Embodiment 20 | | linear octyl group | | 7.5 |
| Embodiment 21 | | linear nonyl group | | 8.0 |
| Embodiment 22 | | linear decyl group | | 8.2 |
| Embodiment 23 | | linear undecyl group | | 10.0 |
| Embodiment 24 | | linear dodecyl group | | 12.0 |

Note:
The dissolution temperature of the para-phenylenediamine derivative (Comparative Example 1 and Embodiments 1-12) is 50° C., and the dissolution temperature of the 1,4-cyclohexanediamine derivative (Comparative Example 2 and Embodiments 13-24) is 70° C.

Figure 2:
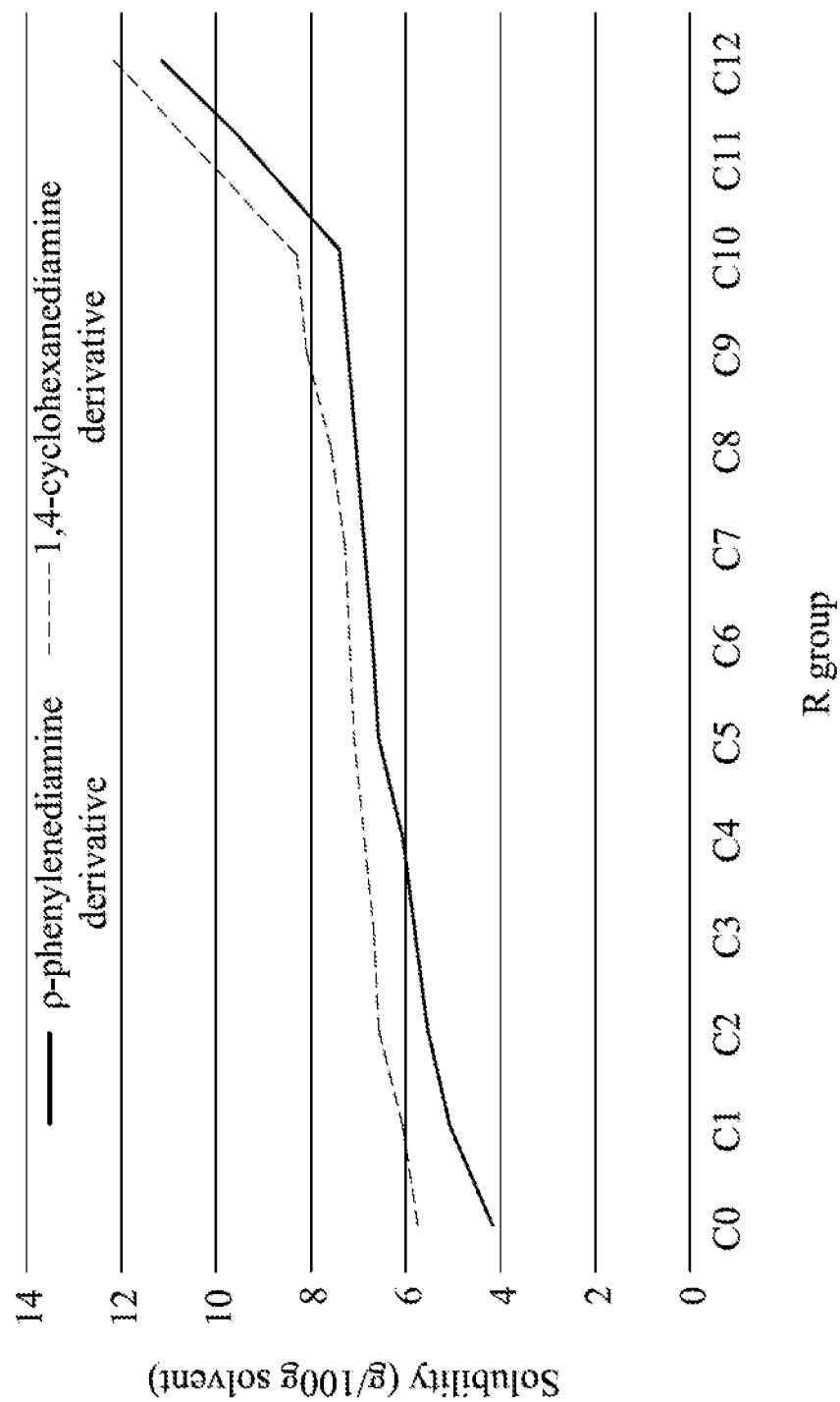
FIG. 2 illustrates a trend in solubility of the para-phenylenediamine derivative and the 1,4-cyclohexanediamine derivative according to some embodiments of the present disclosure.

It can be seen from the data of Comparative Examples 1-2 that when the compound does not have the R group described above (that is, the compound is para-phenylenediamine or 1,4-cyclohexanediamine), the solubility of the compound in the solvent is very low, which is not conducive to the subsequent polymerization reaction. It can be seen from Embodiments 1-12 and 13-24 that when the R group of the compound is a linear alkyl group, the solubility of the compound in the solvent can be effectively improved. Furthermore, it can be seen from Embodiments 11-12 and 23-24 that when the R group of the compound is a linear alkyl group, and the carbon number of the linear alkyl group is greater than or equal to 11, the solubility of the compound in the solvent is greatly improved, thereby facilitating the subsequent polymerization reaction to increase the molecular weight of the polymer. In more detail, please refer to FIG. 2, which illustrates a trend in solubility of the para-phenylenediamine derivative and the 1,4-cyclohexanediamine derivative according to some embodiments of the present disclosure. It can be clearly seen from FIG. 2 that when the carbon number of the linear alkyl group gradually increases from 1 to 10, the solubility of the compound gradually increases, and when the carbon number of the linear alkyl group gradually increases from 10 to 12, the solubility of the compound is significantly improved (that is, the slope of the curve is significantly increased), indicating that when the carbon number of the linear alkyl group is greater than or equal to 11, the para-phenylenediamine derivative and the 1,4-cyclohexanediamine derivative have excellent solubility.

In summary, the present disclosure provides a para-phenylenediamine derivative and a 1,4-cyclohexanediamine derivative, which can be applied to the field of flexible displays to play the role of monomers of polymers. Through the respective molecular structure designs of the para-phenylenediamine derivative and the 1,4-cyclohexanediamine derivative (e.g., the design of the R group), the para-phenylenediamine derivative and the 1,4-cyclohexanediamine derivative can have good solubility to facilitate the subsequent polymerization reaction. On the other hand, the present disclosure further provides a fabricating method for a 1,4-diamine cyclic compound derivative, by which the para-phenylenediamine derivative or the 1,4-cyclohexanediamine derivative can be selectively obtained through the control of the reaction conditions. Accordingly, the desired product (the para-phenylenediamine derivative or the 1,4-cyclohexanediamine derivative) can be selectively obtained through the switching of reaction conditions in a single fabricating method, such that the convenience of fabricating monomers is improved, and the production costs are reduced.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. A 1,4-cyclohexanediamine derivative, having a structure represented by formula (II):

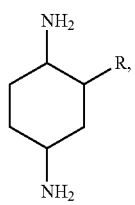

formula (II)

wherein R represents a C5 to C12 linear alkyl group.

2. A fabricating method for a 1,4-diamine cyclic compound derivative, comprising:
performing a first thermal process which comprises using monohydric alcohol and ρ-toluenesulfonic acid for an addition reaction of ρ-nitroacetaniline, such that a first compound is formed, wherein the monohydric alcohol has a C1 to C12 hydrocarbon group, and the first compound has a structure represented by formula (i):

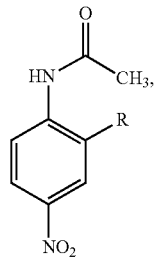

formula (i)

wherein R represents a C1 to C12 hydrocarbon group;
performing a second thermal process which comprises performing a reduction reaction on the first compound, such that a second compound is formed, wherein the second compound has a structure represented by formula (ii),

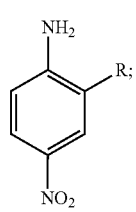

formula (ii)

and
performing a third thermal process which comprises performing a reduction reaction on the second compound, such that the 1,4-diamine cyclic compound derivative is formed, wherein the 1,4-diamine cyclic compound derivative has a structure represented by formula (I) or formula (II):

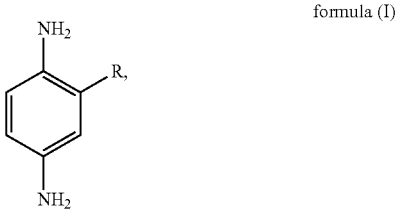

formula (I)

wherein R represents a C1 to C12 hydrocarbon group,

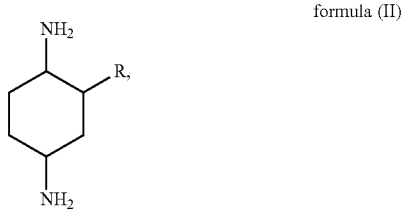

formula (II)

wherein R represents a C1 to C12 hydrocarbon group.

3. The fabricating method for a 1,4-diamine cyclic compound derivative of claim 2, wherein the third thermal process comprises using hydrogen to perform the reduction reaction on the second compound, and when the 1,4-diamine cyclic compound derivative has the structure represented by formula (I), a pressure of the third thermal process is between 14 psi and 15 psi, a temperature of the third thermal process is between 25° C. and 40° C., and based on 1 equivalence of the second compound, an equivalence of the hydrogen is between 2.5 and 4.

4. The fabricating method for a 1,4-diamine cyclic compound derivative of claim 2, wherein the third thermal process comprises using hydrogen to perform the reduction reaction on the second compound, and when the 1,4-diamine cyclic compound derivative has the structure represented by formula (II), a pressure of the third thermal process is between 600 psi and 800 psi, a temperature of the third thermal process is between 100° C. and 140° C., and based on 1 equivalence of the second compound, an equivalence of the hydrogen is between 7 and 8.

5. The fabricating method for a 1,4-diamine cyclic compound derivative of claim 2, wherein based on 1 equivalence of the p-nitroacetaniline, an equivalence of the p-toluenesulfonic acid is between 1.1 and 1.5.

* * * * *